US00PP11494P

United States Patent [19]

Olij

[11] Patent Number: Plant 11,494

[45] Date of Patent: Aug. 22, 2000

[54] HYBRID TEA ROSE PLANT NAMED 'OLIJGLU'

[75] Inventor: Huibert W. Olij, De Kwakel, Netherlands

[73] Assignee: Olij Rozen B.V., PP de Kwakel, Netherlands

[21] Appl. No.: 09/150,090

[22] Filed: Sep. 9, 1998

[51] Int. Cl.[7] ..... A01H 5/00

[52] U.S. Cl. ..... Plt./130

[58] Field of Search ..... Plt./135, 137, 130, Plt./132

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which abundantly forms attractive blossoms which are a blend of pink, cream and green and exhibit a long vase life. The buds are large, and are borne on erect stems. Attractive semi-glossy dark green foliage is formed, and the plant exhibits very good disease resistance. The new variety is particularly well suited for forming cut flowers on a highly productive basis under greenhouse growing conditions.

1 Drawing Sheet

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) of the new variety was the 'Ruirovingt' variety (U.S. Plant Pat. No. 8,528). The male parent (i.e., the pollen parent) was the product of the crossing of the 'Meibrimel' variety (non-patented in the United States) and the 'Olytel' variety (U.S. Plant Pat. No. 8,862). The parentage of the new variety can be summarized as follows:

'Ruirovingt'×('Meibrimel'×'Olytel').

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms attractive large buds on erect stems,
(b) forms in abundance attractive blossoms which exhibit a long vase life that are a blend of pink, cream, and green,
(c) forms attractive semi-glossy dark green foliage,
(d) exhibits very good disease resistance with respect to powdery mildew and downy mildew, and
(e) is particularly well suited for the production of cut flowers under greenhouse growing conditions.

The new variety of the present invention can be readily distinguished from its parent varieties. For instance, the 'Ruirovingt' variety forms smaller blossoms that are salmon pink in coloration. The 'Meibrimel' variety exhibits yellow and red bicolored blossoms and the 'Olytel' variety also forms bicolored blossoms that are unlike those of the present variety.

The new variety well meets the needs of the horticultural industry and exhibits good productivity during cut flower production in a greenhouse.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Olijglu' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during April while budded on *Rosa indica* understock and growing in greenhouses at Le Cannet des Maures, Var, France. Dimensions in centimeters are indicated at the bottom of the photograph. Page No. 62 from the R.H.S. Colour Chart of The Royal Horticultural Society is shown at the lower-left portion of the photograph for comparative purposes.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of a leaf with three leaflets — plan view — upper surface; and FIG. 15 — illustrates a specimen of a leaf with five leaflets — plan view — under surface.

DETAILED DESCRIPTION

Figures 1, 2, 3, 4, 5, 6, 7, 8, 9, 10, 11, 12, 13, 14, 15:
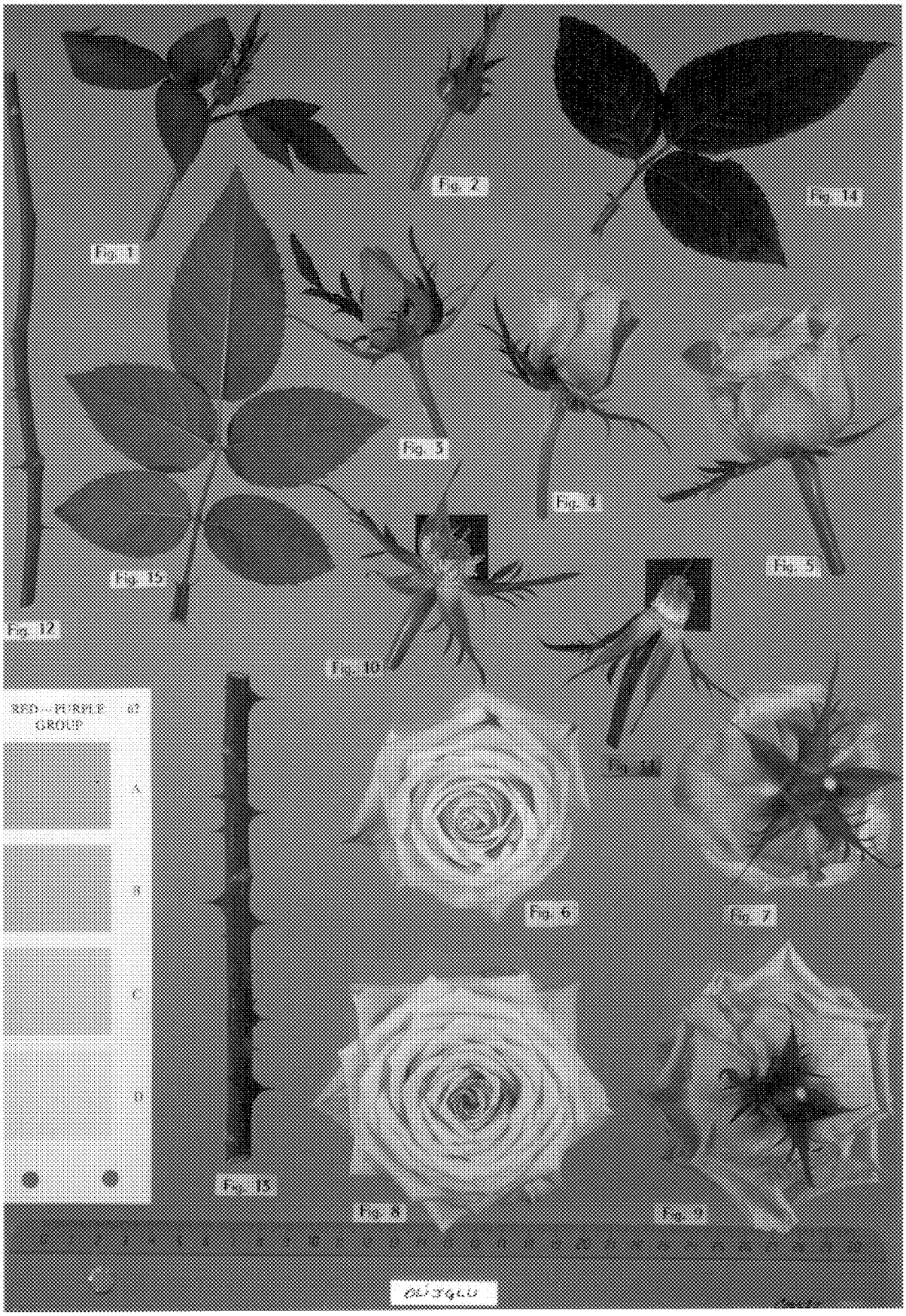

The chart used in the identification of the colors is that of The Royal Horticultural Society (R.H.S. Colour Chart). The description is based on the observation of two year-old plants during April while budded on *Rosa indica* understock and growing indoors at Le Cannet des Maures, Var, France. The coloration in common terms precedes reference to the chart in some instances.

Class: Hybrid tea.

Plant: *Height.*—When pruned to a height of 85 cm., floral stems of approximately 70 to 90 cm. in length commonly are produced.

*Habit.*—Erect.

Branches:

*Color.*—Young stems: Yellow-Green Group 144C in coloration. Adult wood: Yellow-Green Group 146B in coloration.

*Thorns.*—Size: Medium (as illustrated). Quantity: Moderately numerous. Color: Near Yellow-Green Group 148A changing to Greyed-Orange Group 166D upon maturity.

Leaves:

*Stipules.*—Adnate, pectinate, and narrow.

*Petioles.*—Upper surface: Near Green Group 137A with a few glands. Under surface: Greyed-Green Group 191B with some prickles.

*Leaflets.*—Number: 3, 5 (most often), and 7. Shape: Elliptic. Serration: Single and regular (as illustrated). Size: Relatively long (as illustrated). Texture: Somewhat consistent. General appearance: Dense, dark green, and semi-glossy. Color (young foliage): Upper surface: Near Green Group 137A with reddish staining. Under surface: Near Greyed-Green Group 191B with reddish staining. Color (adult foliage): Upper surface: Near Green Group 139A. Under surface: Near Greyed-Green Group 191A.

Inflorescence:

*Number of flowers.*—Usually one flower per stem, and may have up to about three flowers per stem.

*Peduncle.*—Light green in coloration, glabrous, and the length is approximately 12 cm. on average.

*Sepals.*—Upper surface: Tomentose and near Green Group 137B in coloration. Under surface: Smooth and commonly with heavy foliation (as illustrated).

*Buds.*—Shape: Ovoid. Size: Large. Length: Approximately 4.5 cm. on average. Color upon opening: Upper surface: Near Greyed-Red Group 179D with greenish reflections. Under surface: Near Red-Purple Group 66C and suffused with near Greyed-Red Group 179D.

*Flower.*—Shape: Commonly with a high center. Diameter: Commonly approximately 12 cm. on average. Petal number: Approximately approximately 81 to 87 average. Color (when opening begins): Upper surface: Near Red-Purple Group 62D with some yellowish (near Yellow Group 8D) and green (near Yellow-Green Group 144A) coloration. Under surface: Near Red-Purple Group 68D suffused with near Red-Purple Group 67B with some greenish small veins. Color (when blooming): Upper surface: Near Red-Purple Group 62D with some coloration near Red-Purple Group 63lB and suffused with Yellow-Orange Group 23D. Under surface: Near Red-Purple Group 64D suffused with some near Red-Purple Group 65B with some whitish small veins. Color (at end of opening): Upper surface: near Orange Group 29D suffused with near Orange Group 27D. Under surface: Near Red Group 54D with some whitish small veins. Fragrance: Woodsy. Lasting quality: Very good, approximately 10 to 12 days on the plant and approximately 9 to 11 days when cut and placed in a vase. Petal shape: Rounded, with reflexed edges and some quilling. Petal drop: Good, the petals commonly detach cleanly. Stamen number: Approximately 216 on average. Anthers: Yellow in coloration. Filaments: Yellow-orange in coloration. Pollen: Present, and has been infertile when crosses have been attempted to date. Pistils: Approximately 118 on average. Stigmas: Havana brown in coloration. Styles: Dark pink in coloration. Receptacle: Light green in coloration, and in longitudinal section in the shape of a funnel.

Development:

*Vegetation.*—Vigorous.

*Blooming.*—Very Abundant. Commonly approximately 110 to 140 blossoms are formed per square meter per year under greenhouse growing conditions.

*Resistance to diseases.*—Very good with respect to powdery mildew and downy mildew.

I claim:

1. A new and distinct variety of Hybrid Tea rose plant characterized by the following combination of characteristics:

(a) forms attractive large buds on erect stems,
(b) forms in abundance attractive blossoms which exhibit a long vase life that are a blend of pink, cream, and green,
(c) forms attractive semi-glossy dark green foliage,
(d) exhibits very good disease resistance with respect to powdery mildew and downy mildew, and
(e) is particularly well suited for the production of cut flowers under greenhouse growing conditions;

substantially as herein shown and described.

* * * * *

RED—PURPLE GROUP
62
A
B
C
D